United States Patent [19]

Katakami et al.

[11] Patent Number: 4,539,150
[45] Date of Patent: Sep. 3, 1985

[54] BENZOTHIAZEPINE DERIVATIVES AND THEIR METHODS OF PREPARATION

[75] Inventors: Tsutomu Katakami; Nobuyuki Fukazawa, both of Yokohama; Hajime Iizuka, Hiratsuka; Takashi Nishina; Isao Shirakawa, both of Mobara, all of Japan

[73] Assignee: Mitsui Toatsu Chemicals, Inc., Tokyo, Japan

[21] Appl. No.: 625,656

[22] Filed: Jun. 28, 1984

[30] Foreign Application Priority Data

Jun. 29, 1983 [JP] Japan ................. 58-116177
Aug. 8, 1983 [JP] Japan ................. 58-143655
Sep. 27, 1983 [JP] Japan ................. 58-177001
Nov. 18, 1983 [JP] Japan ................. 58-216058

[51] Int. Cl.³ .......................................... C07D 281/02
[52] U.S. Cl. .................................... 260/239.3 B
[58] Field of Search ......................... 260/239.3 B

[56] References Cited

FOREIGN PATENT DOCUMENTS 2103614A 2/1983 United Kingdom ......... 260/239.3 B

Primary Examiner—Robert T. Bond
Attorney, Agent, or Firm—Fisher, Christen & Sabol

[57] ABSTRACT

This invention relates to benzothiazepine derivatives of the general formula

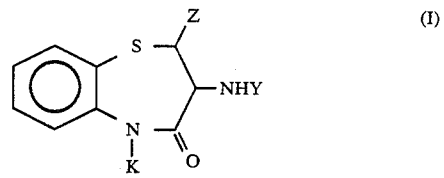

where K is hydrogen or a —$CH_2COOR_2$ group where $R_2$ is hydrogen or a lower alkyl group, Z is hydrogen or phenyl except when both K and Z are hydrogen, and Y is hydrogen, a —$CHR_3$—$COOR_1$ group, an alkanoyl group or a —$COO(CH_2)_nR_4$ group where $R_1$ is hydrogen or a lower alkyl group, $R_3$ is hydrogen, an alkyl group, an alkylphenyl group or an aryl-lower alkyl group, $R_4$ is an aryl group and n is a whole number of 1 to 10, and to their methods of preparation.

The benzothiazepine derivatives of this invention, including their salts, have a powerful inhibitory effect on the angiotensin converting enzyme and exert a marked depressor effect in such models of hypertension as spontaneously occurring hypertensive rats and the like, so that they are useful as drugs for the treatment of hypertension and other cardiovascular diseases. In addition, these compounds are also useful as intermediates for the synthesis of coronary dilators, psychotropic drugs and the like.

9 Claims, No Drawings

BENZOTHIAZEPINE DERIVATIVES AND THEIR METHODS OF PREPARATION

BACKGROUND OF THE INVENTION

1. Field of the Invention

This invention relates to novel benzothiazepine derivatives and their methods of preparation.

2. Description of the Prior Art

It is generally known that angiotensin present in the blood acts on the smooth muscle of blood vessels to cause an intense contraction thereof and hence a marked rise in blood pressure. There are two forms of angiotensin: angiotensin I and angiotensin II. Renin, which is secreated by the kidneys, acts on angiotensinogen to form angiotensin I. By the action of the angiotensin converting enzyme present in blood plasma and tissues, angiotensin I is converted into angiotensin II. It is angiotensin II that has biological activities.

A rise in blood pressure could be checked by inhibiting the angiotensin converting enzyme from acting on angiotensin I. With attention focused on this idea, the development of compounds which are useful as drugs for the treatment of hypertension and other cardiovascular diseases has hitherto been carried on.

However, there have been obtained no compounds that are entirely satisfactory from the viewpoints of efficacy, side effects, toxicity and the like. Therefore, it would be still desirable to develop such compounds.

Moreover, pharmaceutical applications require that the desired compounds can be consistently produced in high yield and readily separated from by-products and the like.

SUMMARY OF THE INVENTION

It is an object of the present invention to provide novel compounds which have an inhibitory effect on the activity of angiotensin while exhibiting little toxicity.

It is another object of the present invention to provide novel compounds which are useful as drugs for the treatment of hypertension and other cardiovascular diseases.

It is still another object of the present invention to provide several processes for preparing such compounds.

According to the present invention, there are provided benzothiazepine derivatives of the general formula

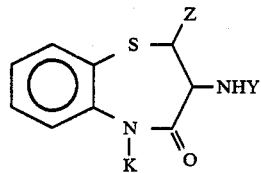

(I)

where K is hydrogen or a —$CH_2COOR_2$ group where $R_2$ is hydrogen or a lower alkyl group, Z is hydrogen or phenyl except when both K and Z are hydrogen, and Y is hydrogen, a —$CHR_3$—$COOR_1$ group, an alkanoyl group or a —$COO(CH_2)_nR_4$ group where $R_1$ is hydrogen or a lower alkyl group, $R_3$ is hydrogen, an alkyl group, an alkylphenyl group or an aryl-lower alkyl group, $R_4$ is an aryl group and n is a whole number of 1 to 10.

DETAILED DESCRIPTION OF THE INVENTION

The benzothiazepine derivatives of the present invention will be more fully described hereinbelow.

In the general formula (I), the lower alkyl groups represented by $R_1$ and $R_2$ are selected from the group consisting of methyl, ethyl, propyl, isopropyl, butyl, sec-butyl, t-butyl and the like. The alkanoyl group represented by Y is selected from the group consisting of formyl, acetyl, propanoyl, butanoyl, pivaloyl and the like. The alkyl group represented by $R_3$ is preferably a straight-chain or branched alkyl group having 1 to 10 carbon atoms, and specific examples thereof include methyl, ethyl, propyl, isopropyl, butyl, isobutyl, pentyl, hexyl, heptyl, octyl, nonyl, decyl and the like. In benzothiazepine derivatives as claimed in claim 5, a straight-chain or branched alkyl group having 5 to 10 carbon atoms is most preferably used as the alkyl group represented by $R_3$. The alkylphenyl group represented by $R_3$ has the formula

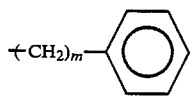

and, among such alkylphenyl groups, those in which m is 1 or 2 (i.e., benzyl and phenetyl) are particularly preferred. The aryl-lower alkyl group represented by $R_3$ is selected from the group consisting of tolylmethyl, tolylethyl, tolylpropyl, tolylbutyl, xylylmethyl, xylylethyl, xylylpropyl, xylylbutyl and the like. As the —$COO(CH_2)_nR_4$ group represented by Y, those in which n is a whole number of 1 to 5 are particularly preferred. Specific examples thereof include benzyloxycarbonyl, phenetyloxycarbonyl, phenylpropyloxycarbonyl, phenylbutyloxycarbonyl, phenylpentyloxycarbonyl, tolylmethoxycarbonyl, tolylethoxycarbonyl, tolylpropoxycarbonyl, tolylbutoxycarbonyl, tolylpentyloxycarbonyl, xylylmethoxycarbonyl, xylylethoxycarbonyl, xylylpropoxycarbonyl, xylylbutoxycarbonyl, xylylpentyloxycarbonyl and the like.

Typical benzothiazepine derivative falling within the scope of the present invention include:
- 3-amino-2-phenyl-2,3-dihydro-1,5-benzothiazepin-4(5H)-one,
- 3-benzyloxycarbonylamino-2-phenyl-2,3-dihydro-1,5-benzothiazepin-4(5H)-one,
- 3-amino-5-ethoxycarbonylmethyl-2,3-dihydro-1,5-benzothiazepin-4(5H)-one,
- 3-amino-5-t-butoxycarbonylmethyl-2,3-dihydro-1,5-benzothiazepin-4(5H)-one,
- 5-carboxymethyl-3-carboxymethylamino-2,3-dihydro-1,5-benzothiazepin-4(5H)-one,
- 5-carboxymethyl-3-ethoxycarbonylmethylamino-2,3-dihydro-1,5-benzothiazepin-4(5H)-one,
- 3-ethoxycarbonylmethylamino-5-t-butoxycarbonylmethyl-2,3-dihydro-1,5-benzothiazepin-4(5H)-one,
- 5-carboxymethyl-3-(1-carboxyethylamino)-2,3-dihydro-1,5-benzothiazepin-4(5H)-one,
- 5-carboxymethyl-3-(1-carboxynonylamino)-2,3-dihydro-1,5-benzothiazepin-4(5H)-one,
- 5-carboxymethyl-3-(1-ethoxycarbonylethylamino)-2,3-dihydro-1,5-benzothiazepin-4(5H)-one,
- 5-carboxymethyl-3-(1-ethoxycarbonylnonylamino)-2,3-dihydro-1,5-benzothiazepin-4(5H)-one, 5-t-butoxycarbonylmethyl-3-(1-ethoxycarbonyle-thylamino)-2,3-dihydro-1,5-benzothiazepin-4(5H)-one 3-(1-ethoxycarbonylnonylamino)-5-t-butoxycarbonylmethyl-2,3-dihydro-1,5-benzothiazepin-4(5H)-one, 3-(1-carboxy-3-phenylpropylamino)-5-carboxymethyl-2,3-dihydro-1,5-benzothiazepin-4(5H)-one, 5-carboxymethyl-3-(1-ethoxycarbonyl-3-phenylpropylamino)-2,3-dihydro-1,5-benzothiazepin-4(5H)-one, 3-(1-ethoxycarbonyl-3-phenylpropylamino)-5 ethoxycarbonylmethyl-2,3-dihydro-1,5-benzothiazepin-4(5H)-one, 3-amino-5-t-butoxycarbonylmethyl-2-phenyl-2,3-dihydro-1,5-benzothiazepin-4(5H)-one, 5-carboxymethyl-3-carboxymethylamino-2-phenyl-2,3-dihydro-1,5-benzothiazepin-4(5H)-one, 5-carboxymethyl-3-ethoxycarbonylmethylaminophenyl-2,3-dihydro-1,5-benzothiazepin-4(5H)-one, 5-t-butoxycarbonylmethyl-3-ethoxycarbonylmethylamino-2-phenyl-2,3-dihydro-1,5-benzothiazepin-4(5H)-one, 5-carboxymethyl-3-(1-carboxynonylamino)-2-phenyl-2,3-dihydro-1,5-benzothiazepin-4(5H)-one, 5-carboxymethyl-3-(1-ethoxycarbonylnonylamino)-phenyl-2,3-dihydro-1,5-benzothiazepin-4(5H)-one, 5-t-butoxycarbonylmethyl-3-(1-ethoxycarbonylnonylamino)-2-phenyl-2,3-dihydro-1,5-benzothiazepin-4(5H)-one, 3-(1-carboxy 3-phenylpropylamino)-3-carboxymethyl-2-phenyl-2,3-dihydro-1,5-benzothiazepin-4(5H)-one, 5-carboxymethyl-3-(1-ethoxycarbonylmethyl-3-phenylpropylamino)-2-phenyl-2,3-dihydro-1,5-benzothiazepin-4(5H)-one, 5-t-butoxycarbonylmethyl-3-(1-ethoxycarbonyl-3-phenylpropylamino)-2-phenyl-2,3-dihydro-1,5-benzothiazepin-4(5H)-one and the like.

The compounds of the present invention can be prepared according to either of the following processes.

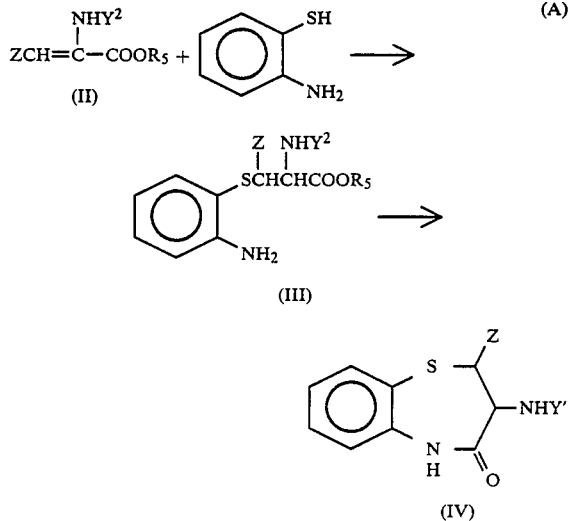

where Z is hydrogen or phenyl, X is a halogen, $Y^2$ is an alkanoyl group, $-COO(CH_2)_nR_4$ group where $R_4$ is a aryl group and n is a whole number of 1 to 10, or an ordinary amino-protecting group, $R_5$ is hydrogen or a lower alkyl group, Y" is hydrogen, an alkanoyl group, a $-COO(CH_2)_nR_4$ group where $R_4$ is an aryl group and n is a whole number of 1 to 10, or an ordinary amino-protecting group.

The term "ordinary amino-protecting group" as used herein comprehends urethane type protecting groups such as p-methoxybenzyloxycarbonyl, p-chlorobenzyloxycarbonyl, p-nitrobenzyloxycarbonyl, 3,5-dimethoxybenzyloxycarbonyl, 3,4,5-trimethoxybenzyloxycarbonyl, t-butoxycarbonyl, etc.; and acyl type protecting groups such as trifluoroacetyl, trichloroacetyl, benzoyl and the like.

Specifically, a compound of the general formula (II) is reacted with 2-aminobenzenethiol at a temperature ranging from 0° C. to the boiling point of the reaction mixture, for a period of several hours. This reaction may be carried out in the absence of solvent or in the presence of a solvent selected from the group consisting of alcohols (such as methanol, ethanol, propanol and the like) and hydrocarbons (such as benzene, toluene, xylene and the like). Thus, there can preferably be obtained a compound of the general formula.

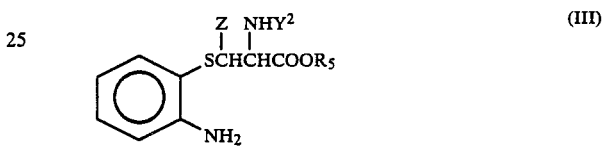

Then, the compound of the general formula (III) can preferably be converted into a compound of the general formula (IV), by heating the former alone or in a suitable solvent such as benzene, toluene, xylene, dimethylformamide, dimethyl sulfoxide, ethylene glycol, diphenyl ether or the like. The same purpose can be accomplished by using a dehydrating agent, such as dicyclohexylcarbodiimide or the like, suitable for cyclizing the compound of the general formula (III) to form the compound of the general formula (IV).

After the compound of the general formula (III) has been cyclized, the alkanoyl, benzyloxycarbonyl or other amino-protecting group may be eliminated from the compound of the general formula (IV), if desired, according to an ordinary procedure for the removal of protecting groups. Thus, there can be obtained a compound of the general formula (IV) in which Y' is hydrogen. For example, where $Y^2$ is benzyloxycarbonyl, this group can be removed by treating the compound with hydrogen bromide-acetic acid, hydrogen bromide-trifluoroacetic acid, hydrogen fluoride or the like, or by dissolving the compound in a suitable solvent such as ethanol, methanol, acetic acid or the like and hydrogenating it at a hydrogen pressure ranging from atmospheric pressure to 100 kg/cm², in the presence of a noble metal catalyst commonly used for hydrogenation, such as palladium-carbon, platinum-carbon, platinum oxide or the like.

If desired, the compound of the general formula (IV) thus obtained may be combined with hydrochloric acid, hydrobromic acid and the like to form their salts.

The compound of the general formula (IV) in accordance with the present invention contains two asymmetric carbon atoms in the nolecule and, therefore, has various optical isomers. It is to be understood that all of such optical isomers fall within the scope of the present invention.

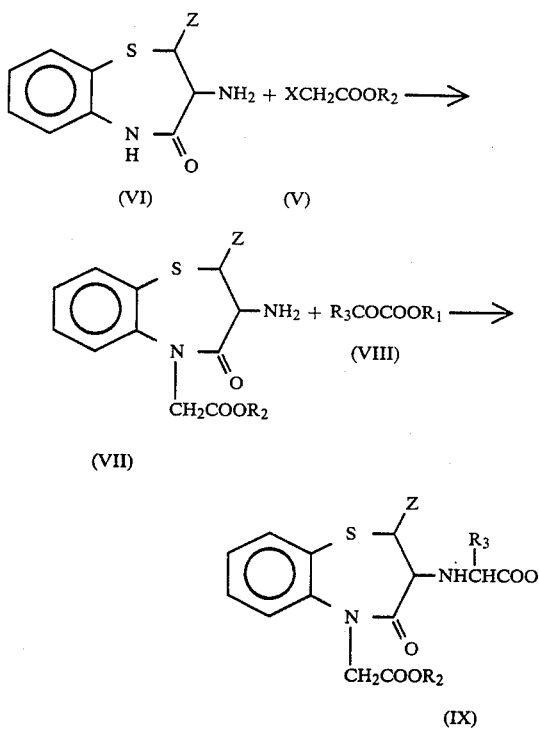

(B)

(VI)    (V)

(VII)

where X and Z are as previously defined, $R_1$ is hydrogen or a lower alkyl group, $R_2$ is hydrogen or a lower alkyl group, and $R_3$ is hydrogen, an alkyl group, an alkylphenyl group or an aryl-lower alkyl group.

Specifically, a compound of the general formula (VI) is reacted with a compound of the general formula (V) in a solvent such as benzene, toluene, xylene, dimethylformamide, dimethyl sulfoxide or the like, in the presence of a suitable desalting agent such as sodium, sodium hydride, potassium hydride, sodium methoxide, sodium ethoxide, potassium t-butoxide or the like. This reaction may be carried out at a temperature ranging from −5° C. to the boiling point of the reaction mixture, for a period of time ranging from about 0.5 to 5 hours. Thus, there can be obtained a compound of the general formula

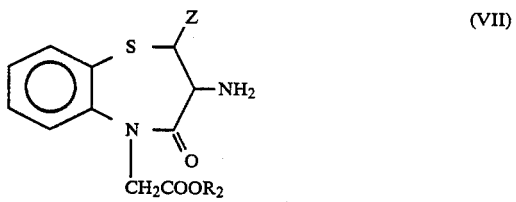

(VII)

where $R_2$ is a lower alkyl group, the compound of the general formula (VII) can be converted into the corresponding carboxylic acid by hydrolyzing the former according to a suitable procedure (for example, saponification by means of alkali). Moreover, where $R_2$ is t-butyl, the compound of the general formula (VII) can also be converted into the corresponding carboxylic acid by reacting the former with an unprotecting agent commonly used for the synthesis of peptides, such as hydrogen chloride-dioxane, hydrogen bromide-acetic acid, or the like.

The benzothiazepine derivative of the general formula (V) which is used as one of the starting materials in this process may be prepared according to the above-described processes (A).

Then, the compound of the general formula (VII) is reacted with a compound of the general formula (VIII) in the presence of a suitable reducing agent to form a compound of the general formula (IX).

More specifically, this reaction is carried out as follows: Under cooling with ice or at a temperature up to 80° C., the compound of the general formula (VII) and the compound of the general formula (VIII) are mixed in a solvent selected from the group consisting of aliphatic or cyclic ethers (such as diethyl ether, dioxane, tetrahydrofuran and the like), alcohols (such as methanol, ethanol, isopropyl alcohol, diethylene glycol, etc.), water and mixtures thereof. Then, these compounds are reduced with a reducing agent to form a compound of the general formula (IX). Suitable reducing agents are complex metal hydrides such as diborane, sodium boron hydride, sodium boron cyanide hydride and the like. The same purpose can be accomplished by hydrogenating the compounds in the presence of a catalyst commonly used for hydrogenation, such as palladium-carbon, platinum-carbon, Raney nickel, Raney copper or the like. In this case, the hydrogenation may be carried out at a hydrogen pressure ranging from 1 to 300 atmospheres and a temperature ranging from room temperature to 150° C. There may be used any of solvents commonly used for hydrogenation, such as water, alcohols (such as methanol, ethanol and the like), acetic acid, ethyl acetate and the like.

Where $R_1$ or $R_2$ is an alkyl group, the compound of the general formula (IX) can be converted into the corresponding carboxylic acid by hydrolyzing the former according to an ordinary procedure (for example, treatment with an alkali). Moreover, where $R_1$ or $R_2$ is t-butyl, the compound of the general formula (IX) can also be converted into the corresponding carboxylic acid, simply by exposing the former to an ordinary reagent for the cleavage of t-butyl esters, such as hydrogen chloride-dioxane, hydrogen bromide-acetic acid or the like.

The compound of the general formula (IX) in accordance with the present invention contains three asymmetric carbon atoms in the molecule and, therefore, has various stereoisomers. It is to be understood that all of such stereoisomers fall within the scope of the present invention.

The compound of the general formula (IX) thus obtained may contain one or two carboxyl groups in the molecule. In this case, the compound of the general formula (IX) can be combined with various inorganic or organic bases to form its salts. Specific examples of such salts include metallic salts such as sodium, potassium, calcium, magnesium and like salts; and salts formed with organic bases such as lysine, dicyclohexylamine and like salts. Moreover, the compound of the general formula (IX) contains an amino group that can combine with various acids to form salts. For example, the compound of the general formula (IX) can be combined with inorganic and organic acids, such as hydrochloric acid, hydrobromic acid, tartaric acid, maleic acid and the like, to form its salts.

The benzothiazepine derivatives of the present invention, including their salts formed as above, have a powerful inhibitory effect on the angiotensin converting enzyme and exert a marked depressor effect in such models of hypertension as spontaneously occurring hypertensive rats and the like, so that they are useful as drugs for the treatment of hypertension and other cardiovascular diseases. In addition, these compounds are also useful as intermediates for the synthesis of coronary dilators, psychotropic drugs and the like.

The present invention is further illustrated by the following examples. However, these examples are not to be construed to limit the scope of the invention.

EXAMPLE 1

Preparation of N-benzyloxycarbonyl-S-(2-aminophenyl)-β-phenylcysteine 20 g of α-benzyloxycarbonylamino-β-phenylacrylic acid and 10 g of o-aminobenzenethiol were mixed with 40 ml of ethanol and the resulting mixture was heated under reflux for 20 hours. After cooling to room temperature, the precipitated crystalline component was separated by filtration and washed with ethanol to obtain 2.7 g of crystals. This product decomposed at 198° C.

EXAMPLE 2

Preparation of 3-benzyloxycarbonylamino-2-phenyl-2,3-dihydro-1,5-benzothiazepin-4(5H)-one 2.7 g of the N-benzyloxycarbonyl-S-(2-aminophenyl)-β-phenylcysteine obtained in Example 1 was suspended in 60 ml of xylene and the resulting suspension was heated under reflux for 3 hours. Thereafter, the apparatus was cooled to room temperature. The precipitated crystals were separated by filtration and washed with ethanol to obtain 1.9 g of the desired compound. This compound had a melting point of 246°–248° C.

EXAMPLE 3

Preparation of 3-amino-2-phenyl-2,3-dihydro-1,5-benzothiazepin-4(5H)-one hydrobromide 5.4 g of the compound obtained in Example 2 was dissolved in a 25% solution of hydrogen bromide in acetic acid. After the lapse of 2 hours, 15 ml of acetic acid was added to the solution and the resulting mixture was stirred for an hour. After the addition of ether, the precipitated crystals were separated by filtration and washed with ether to obtain 4.0 g of the desired compound.

This compound had a melting point of 300° C. or above.

Its infrared (IR) absorption spectrum (as measured in a KBr tablet) exhibited an absorption band characteristic of C=O at 1670 cm$^{-1}$.

EXAMPLE 4

Preparation of 3-amino-2-phenyl-2,3-dihydro-1,5-benzothiazepin-4(5H)-one 1.5 g of the compound obtained in Example 2 was dissolved in 70 ml of methanol and then hydrogenated at atmospheric pressure in the presence of 100 mg of 5% palladium-carbon.

After the absorption of hydrogen stopped, the catalyst was filtered off and the resulting methanol solution was concentrated to obtain the desired compound, or 3-amino-2-phenyl-2,3-dihydro-1,5-benzothiazepin-4(5H)-one. To this compound were added a 25% solution of hydrogen bromide in acetic acid and then ether. The precipitated crystals were separated by filtration and washed with ether to obtain 3-amino-2-phenyl-2,3-dihydro-1,5-benzothiazepin-4(5H)-one hydrobromide. The infrared spectrum and melting point of this product agreed with those of the compound obtained in Example 3.

EXAMPLE 5

Preparation of 3-benzyloxycarbonylamino-2-phenyl-2,3-dihydro-1,5-benzothiazepin-4(5H)-one The compound obtained in Example 2 was prepared according to an alternative procedure.

1.0 g of N-benzyloxycarbonyl-S-(2-aminophenyl)-β-phenylcysteine was mixed with 0.5 g of dicyclohexylcarbodiimide and 15 ml of N,N-dimethylformamide and the resulting mixture was stirred for 5 hours. After the mixture was concentrated under reduced pressure, 20 ml of ethyl acetate was added to the residue and the insoluble matter was removed. Thereafter, the solution was concentrated to obtain the desired compound, or 3-benzyloxycarbonylamino-2-phenyl-2,3-dihydro-1,5-benzothiazepin-4(5H)-one. The physical properties of this product agreed with those of the compound obtained in Example 2.

EXAMPLE 6

Preparation of 3-amino-5-ethoxycarbonylmethyl-2,3-dihydro-1,5-benzothiazepin-4(5H)-one hydrochloride 2.0 g of 3-amino-2,3-dihydro-1,5-benzothiazepin-4(5H)-one hydrobromide was dissolved in 30 ml of dimethylformamide, and 600 mg of sodium hydride (in the form of a 60% suspension in oil) was added thereto. After the mixture was stirred at 50° C. for 15 minutes, a solution of 1.21 g of ethyl bromoacetate in 5 ml of dimethylformamide was added thereto and the resulting mixture was stirred at 50° C. for 3 hours. After the solvent was distilled off, benzene was added to the residue and the insoluble matter was filtered off. The filtrate was concentrated under reduced pressure and the resulting oily material was dissolved in ether. Then, hydrogen chloride-ether was added to the solution so as to cause crystallization. Thus, there was obtained 1.97 g of the desired compound. When heated to determine its melting point, this compound decomposed at 218° C.

EXAMPLE 7

Preparation of 3-amino-5-t-butoxycarbonylmethyl-2,3-dihydro-1,5-benzothiazepin-4(5H)-one In the same manner as described in Example 6, t-butyl bromoacetate was reacted with the corresponding benzothiazepine to obtain the desired compound, or 3-amino-5-t-butoxycarbonylmethyl-2,3-dihydro-1,5-benzothiazepin-4(5H)-one. Its melting point was 97°–99° C.

EXAMPLE 8

Preparation of 3-(1-carboxy-3-phenylpropylamino)-5-carboxymethyl-2,3-dihydro-1,5-benzothiazepin-4(5H)-one 1.2 g of 3-(1-ethoxycarbonyl-3-phenylpropylamino)-5-ethoxycarbonylmethyl-2,3-dihydro-1,5-benzothiazepin-4(5H)-one was dissolved in 15 ml of ethanol, and 6 ml of 1N NaOH was added thereto. The resulting mixture was stirred at room temperature, so that white crystals were precipitated. After 1.5 hours, the ethanol was distilled off under reduced pressure and water was added to the residue. After a small amount of insoluble matter was filtered off, the filtrate was adjusted to pH 3–4 with 6N hydrochloric acid. The precipitated crystals were separated by filtration and washed with cold water and then with ether to obtain 650 mg of the desired compound.

The infrared spectrum of this compound exhibited the following characteristic absorption bands:

$IR_{max}^{KBr}$, cm$^{-1}$: 3440, 1740, 1690, 1400, 1220, 760, 710.

EXAMPLE 9

Preparation of 3-(1-ethoxycarbonyl-3-phenylpropylamino)-5-ethoxycarbonylmethyl-2,3-dihydro-1,5-benzothiazepin-4(5H)-one 1.8 g of 3-amino-5-ethoxycarbonylmethyl-2,3-dihydro-1,5-benzothiazepin-4(5H)-one hydrochloride was mixed with 2.5 g of ethyl benzylpyruvate and 30 ml of ethanol, and the resulting mixture was adjusted to pH 5–7 with a saturated aqueous solution of sodium carbonate. After the mixture was allowed to stand for 2 hours, a solution of 0.7 g of sodium boron cyanide hydride in 10 ml of ethanol was added dropwise thereto over a period of one hour. To this mixture were added 5 ml of acetic acid and then 2.5 g of ethyl benzylpyruvate. After 2 hours, 2.0 g of ethyl benzylpyruvate was added and the mixture was allowed to stand overnight. After the ethanol was distilled off, 5 ml of concentrated hydrochloric acid was added to the residue and the resulting mixture was stirred for an hour. After the addition of 80 ml of water, the mixture was extracted with ether. 5 ml of hydrogen chloride-ether was added to the ether extract and the separated oily material was isolated. Further, 10 ml of 6N hydrochloric acid was added to the ether layer, and the resulting mixture was stirred for a while and then allowed to stand. The lower layer was isolated and combined with the previously obtained oily material, followed by washing with ether. The aqueous layer was adjusted to pH 2–3 with a sodium hydroxide solution and then extracted with ether. After drying over anhydrous sodium sulfate, the product was concentrated to obtain 1.28 g of the desired compound in the form of an oily material.

The infrared spectrum (as measured between NaCl plates) of this compound exhibited the following characteristic absorption bands:

$IR_{max}^{NaCl}$, cm$^{-1}$: 1760, 1690, 1490, 1210, 1040, 880, 710.

EXAMPLE 10

Preparation of 5-carboxymethyl-3-(1-ethoxycarbonyl-3-phenylpropylamino)-2,3-dihydro-1,5-benzothiazepin-4(5H)-one hydrochloride The compound obtained in Example 7 was reacted with ethyl benzylpyruvate in the same manner as described in Example 9. Thus, there was obtained 5-t-butoxycarbonylmethyl-3-(1-ethoxycarbonyl-3-phenylpropylamino)-2,3-dihydro-1,5-benzothiazepin-4(5H)-one in the form of an oily material.

15 ml of a solution of hydrogen chloride in dioxane was added to 4.5 g of the above diester and the resulting mixture was stirred for 2 hours. After completion of the reaction, the solvent was distilled off under reduced pressure and ether was added to the residue so as to cause crystallization. The precipitated crystals were separated by filtration and washed with ether to obtain 1.65 g of the desired compound, or 5-carboxymethyl-3-(1-ethoxycarbonyl-3-phenylpropylamino)-2,3-dihydro-1,5-benzothiazepin-4(5H)-one hydrochloride. Its infrared spectrum exhibited the following principal absorption bands:

$KR_{max}^{KBr}$, cm$^{-1}$: 3440, 1750, 1690, 1480, 1390, 1220, 760, 710.

EXAMPLE 11

Preparation of 5-t-butoxycarbonylmethyl-3-(1-ethoxycarbonylethylamino)-2,3-dihydro-1,5-benzothiazepin-4(5H)-one 1.5 g of 3-amino-5-t-butoxycarbonylmethyl-2,3-dihydro-1,5-benzothiazepin-4(5H)-one and 2.0 g of ethyl pyruvate were dissolved in 15 ml of ethanol. After the addition of 0.3 ml of acetic acid, the resulting mixture was stirred for 2 hours. Then, a solution of 420 mg of sodium boron cyanide hydride in 8 ml of ethanol was slowly added dropwise thereto. After this mixture was allowed to stand overnight, the solvent was distilled off under reduced pressure and the residue was dissolved in ethyl acetate. The resulting solution was washed with water, dried and then concentrated. The residue was purified by silica gel column chromatography using a 3:1 mixture of benzene and ethyl acetate as the eluent. Thus, there was obtained 1.0 g of the desired compound in the form of an oily material.

When analyzed by thin-layer chromatography (TLC), using an Art 5715 plate (Merck & Co., In; for purposes of TLC, Art 5715 plates were used in all of the following examples) and a 3:1 mixture of benzene and ethyl acetate as the developing solvent, this compound gave two spots having $R_f$ values of 0.5 and 0.6.

EXAMPLE 12

Preparation of 5-carboxymethyl-3-(1-ethoxycarbonylethylamino)-2,3-dihydro-1,5-benzothiazepin-4(5H)-one hydrochloride 0.9 g of the 5-t-butoxycarbonylmethyl-3-(1-ethoxycarbonylethylamino)-2,3-dihydro-1,5-benzothiazepin-4(5H)-one obtained in Example 11 was dissolved in 10 ml of a 6N solution of hydrogen chloride in dioxane and then reacted at room temperature for 30 minutes. After the reaction mixture was concentrated under reduced pressure, ether was added thereto so as to cause crystallization. The precipitated crystals were purified by silica gel column chromatography using a 50:3:5 mixture of chloroform, methanol and acetic acid as the eluent. Thus, there was obtained 400 mg of the desired compound.

The results of its analysis by infrared spectroscopy, nuclear magnetic resonance (NMR) spectroscopy and thin-layer chromatography using a 50:3:5 mixture of chloroform, methanol and acetic acid as the developing solvent were as follows:

$IR_{max}^{KBr}$, cm$^{-1}$: 3440, 1740, 1680, 1480, 1230, 1010.
NMR(DMSO-D$_6$), ppm: 1.0–1.4(6H), 3.2–3.4(2H), 3.7–4.3(5H), 4.6–4.8(1H), 7.2–7.7(4H).
TLC: $R_f$=0.65.

EXAMPLE 13

Preparation of
5-carboxymethyl-3-(1-carboxyethylamino)-2,3-dihydro-1,5-benzothiazepin-4(5H)-one hydrochloride 200 mg of the 5-carboxymethyl-3-(1-ethoxycarbonylethylamino)-2,3-dihydro-1,5-benzothiazepin-4(5H)-one hydrochloride obtained in Example 12 was dissolved in 5 ml of water and 1.5 ml of a 1N aqueous solution of sodium hydroxide and then reacted at room temperature for an hour. Thereafter, the solution was adjusted to pH 1-2 with hydrochloric acid and concentrated to dryness under reduced pressure. Ethanol was added to the residue and the insoluble matter was removed by filtration. After the filtrate was concentrated, ether was added thereto so as to cause crystallization. Thus, there was obtained 150 mg of the desired compound.

The results of its analysis by infrared spectroscopy and nuclear magnetic resonance (NMR) spectroscopy were as follows:

$IR_{max}^{KBr}$, cm$^{-1}$: 3420, 1740, 1670, 1480, 1220, 1110, 770.

NMR(DMSO-D$_6$), ppm: 1.3-1.5(3H), 3.7-4.3(5H), 4.6-4.8(1H), 7.3-7.7(4H).

EXAMPLE 14

Preparation of
3-ethoxycarbonylmethylamino-5-t-butoxy-2,3-dihydro-1,5-benzothiazepin-4(5H)-one 1.2 g of 3-amino-5-t-butoxycarbonylmethyl-2,3-dihydro-1,5-benzothiazepin-4(5H)-one and 5.0 g of ethyl glyoxylate were dissolved in 20 ml of ethanol. After the addition of 0.3 ml of acetic acid, the resulting mixture was stirred for 3 hours. Then, a solution of 400 mg of sodium boron cyanide hydride in 7 ml of ethanol was slowly added dropwise thereto. After this mixture was allowed to stand overnight, it was concentrated under reduced pressure and the residue was dissolved in ethyl acetate. The solution was washed with water, dried and then concentrated. The residue was purified by silica gel column chromatography using a 3:1 mixture of benzene and ethyl acetate as the eluent. Thus, there was obtained 1.0 g of the desired compound in the form of an oily material.

When analyzed by thin-layer chromatography using a 3:1 mixture of benzene and ethyl acetate as the developing solvent, this compound exhibited an $R_f$ value of 0.45.

EXAMPLE 15

Preparation of
5-carboxymethyl-3-ethoxycarbonylmethylamino-2,3-dihydro-1,5-benzothiazepin-4(5H)-one hydrochloride 1.25 g of the 3-ethoxycarbonylmethylamino- 5-t-butoxy-2,3-dihydro-1,5-benzothiazepin-4(5H)-one obtained in Example 14 was dissolved in 10 ml of a 6N solution of hydrogen chloride in dioxane and then reacted at room temperature for an hour. After this solution was concentrated under reduced pressure, ether was added thereto so as to cause crystallization. Thus, there was obtained 720 mg of the desired compound. When heated to determine its melting point, this compound decomposed at 248° C.

The results of its analysis by infrared spectroscopy, nuclear magnetic resonance spectroscopy and thin-layer chromatography using a 3:1:1 mixture of n-butanol, acetic acid and water as the developing solvent were as follows:

$IR_{max}^{KBr}$, cm$^{-1}$: 3060, 2740, 1760, 1680, 1390, 1260, 1030, 780.

NMR(DMSO-D$_6$), ppm: 1.1-1.3(3H), 3.2-4.8(9H), 7.2-7.8(4H).

TLC: $R_f$=0.7.

EXAMPLE 16

Preparation of
5-carboxymethyl-3-carboxymethylamino-2,3-dihydro-1,5-benzothiazepin-4(5H)-one hydrochloride 420 mg of the 5-carboxymethyl-3-ethoxycarbonylmethylamino-2,3-dihydro-1,5-benzothiazepin-4(5H)-one hydrochloride obtained in Example 15 was dissolved in 5 ml of water, 3 ml of ethanol and 3.5 ml of a 1N aqueous solution of sodium hydroxide and then reacted for 2 hours. Thereafter, the solution was adjusted to pH 1-2 with hydrochloric acid and concentrated to dryness under reduced pressure. Ethanol was added to the residue and the insoluble matter was filtered off. After the filtrate was concentrated, ether was added thereto so as to cause crystallization. Thus, there was obtained 350 mg of the desired compound.

The results of its analysis by infrared spectroscopy and thin-layer chromatography using a 3:1:1 mixture of n-butanol, acetic acid and water as the developing solvent were as follows:

$IR_{max}^{KBr}$, cm$^{-1}$: 3440, 2980, 1750, 1680, 1480, 1400, 1220, 780.

TLC: $R_f$=0.4.

EXAMPLE 17

Preparation of
3-(1-ethoxycarbonylnonylamino)-5-t-butoxycarbonylmethyl-2,3-dihydro-1,5-benzothiazepin-4(5H)-one 1.3 g of 3-amino-5-t-butoxycarbonylmethyl-2,3-dihydro-1,5-benzothiazepin-4(5H)-one and 3.0 g of ethyl 2-ketodecanoate were dissolved in 10 ml of ethanol. After the addition of 0.3 ml of acetic acid, the resulting mixture was stirred for 3 hours. Then, a solution of 420 mg of sodium boron cyanide hydride in 7 ml of ethanol was added dropwise thereto. After this mixture was allowed to stand overnight, it was concentrated under reduced pressure and the residue was dissolved in ethyl acetate. The solution was washed with water, dried and then concentrated. The residue was purified by silica gel column chromatography using a 7:1 mixture of benzene and ethyl acetate as the eluent. Thus, there was obtained 1.8 g of the desired compound in the form of an oily material.

When analyzed by thin-layer chromatography using a 6:1 mixture of benzene and ethyl acetate as the developing solvent, this compound exhibited an $R_f$ value of 0.65.

EXAMPLE 18

Preparation of
5-carboxymethyl-3-(1-ethoxycarbonylnonylamino)-2,3-dihydro-1,5-benzothiazepin-4(5H)-one 1.7 g of the 3-(1-ethoxycarbonylnonylamino)-5-t-butoxycarbonylmethyl-2,3-dihydro-1,5-benzothiazepin-4(5H)-one obtained in Example 17 was dissolved in 12 ml of a 6N solution of hydrogen chloride in dioxane and then reacted at room temperature for an hour. After this solution was concentrated under reduced pressure, 0.6 ml of triethylamine was added to the residue. This product was purified by silica gel column chromatography using a 5:2 mixture of benzene and acetic acid as the eluent. Thus, there was obtained 1.1 g of the desired compound in the form of a colorless, transparent oily material.

The results of its analysis by infrared spectroscopy, nuclear magnetic resonance spectroscopy and thin-layer chromatophraphy using a 10:3 mixture of benzene and acetic acid as the developing solvent were as follows:

$IR_{max}^{KBr}$, cm$^{-1}$: 2940, 1750, 1690, 1600, 1490, 1400, 1220, 1030.

NMR(DMSO-$D_6$), ppm: 0.7–1.6(20H), 2.6–3.5(4H), 3.8–4.2(3H), 4.5–4.8(1H), 7.2–7.7(4H).

TLC: $R_f$=0.8.

EXAMPLE 19

Preparation of 5-carboxymethyl-3-(1-carboxynonylamino)-2,3-dihydro-1,5-benzothiazepin-4(5H)-one 690 mg of the 5-carboxymethyl-3-(1-ethoxycarbonyl-nonylamino)-2,3-dihydro-1,5-benzothiazepin-4(5H)-one obtained in Example 18 was dissolved in 10 ml of ethanol and 4 ml of a 1N aqueous solution of sodium hydroxide and then reacted at room temperature for 3 hours. After the reaction mixture was concentrated under reduced pressure, the residue was dissolved in 5 ml of water. This solution was adjusted to pH 2 with hydrochloric acid. The precipitated white crystals were separated by filtration and washed thoroughly with water to obtain 600 mg of the desired compound.

The results of its analysis by infrared spectroscopy, nuclear magnetic resonance spectroscopy and thin-layer chromatography using a 3:1:1 mixture of n-butanol, acetic acid and water as the developing solvent were as follows:

$IR_{max}^{KBr}$, cm$^{-1}$: 3440, 2960, 1740, 1690, 1480, 1400, 1230, 770.

NMR(DMSO-$D_6$), ppm: 0.7–1.0(3H), 1.0–1.6(14H), 2.8–3.2(2H), 3.2–3.6(2H), 4.0–4.3(1H), 4.6–4.9(1H), 7.1–7.7(4H).

TLC: $R_f$=0.85.

EXAMPLE 20

Preparation of 3-amino-5-t-butoxycarbonylmethyl-2-phenyl-2,3-dihydro-1,5-benzothiazepin-4(5H)-one 4.8 g of 3-amino-2-phenyl-2,3-dihydro-1,5-benzothiazepin-4(5H)-one hydrobromide was dissolved in 80 ml of N,N-dimethylformamide. After the addition of 1.2 g of sodium hydride (in the form of a 60% suspension in oil), the resulting mixture was stirred at 50° C. for an hour. Then, a solution of 2.7 g of t-butyl bromoacetate in 10 ml of N,N-dimethylformamide was added and the mixture was stirred at 50° C. for an additional hour. After the solvent was distilled off under reduced pressure, hexane was added to the residue so as to cause crystallization. The product was separated by filtration and washed with ether, with water and then with ether to obtain 4.0 g of the desired compound. This compound had a melting point of 178°–180° C.

EXAMPLE 21

Preparation of 5-t-butoxycarbonylmethyl-3-(1-ethoxycarbonyl-3-phenylpropylamino)-2-phenyl-2,3-dihydro-1,5-benzothiazepin-4(5H)-one 1.2 g of the compound obtained in Example 20 was mixed with 2.0 g of ethyl benzylpyruvate, 20 ml of ethanol and 1 ml of acetic acid and dissolved therein by warming to 40° C. The resulting reaction mixture was stirred for 3 hours. Thereafter, a solution of 400 mg of sodium boron cyanide hydride in 10 ml of ethanol was slowly added dropwise to the reaction mixture, which was then allowed to stand overnight. After the solvent was distilled off under reduced pressure, the residue was dissolved in ethyl acetate. The resulting solution was washed with water, dried over anhydrous sodium sulfate and then concentrated under reduced pressure. The concentrate was fractionated and purified by silica gel column chromatography using a 9:1 mixture of benzene and ethyl acetate as the eluent. Thus, there was obtained 1.66 g of the desired compound.

When analyzed by thin-layer chromatography using a 7:1 mixture of benzene and ethyl acetate as the developing solvent, this compound exhibited an $R_f$ value of 0.7.

EXAMPLE 22

Preparation of 5-carboxymethyl-3-(1-ethoxycarbonyl-3-phenylpropylamino)-2-phenyl-2,3-dihydro-1,5-benzothiazepin-4(5H)-one hydrochloride 1.66 g of the compound obtained in Example 21 was dissolved in 10 ml of a 6N a solution of hydrogen chloride in dioxane, and the resulting solution was stirred at room temperature for an hour. Then, ether was added thereto so as to cause crystallization. The precipitated crystals were separated by filtration and washed with ether to obtain 1.1 g of the desired compound.

The infrared absorption characteristics and nuclear magnetic resonance characteristics of this compound were as follows:

$IR_{max}^{KBr}$, cm$^{-1}$: 1730, 1670, 1470, 1450, 1210, 1020, 700.

NMR(DMSO-$D_6$), ppm: 0.9–1.2(3H), 1.3–2.1(4H).

When analyzed by thin-layer chromatography using a 10:3 mixture of benzene and acetic acid as the developing solvent, this compound gave two spots having $R_f$ value in the vicinity of 0.8.

The above compound is a mixture of diastereomers, which can be separated, if desired.

EXAMPLE 23

Preparation of 3-(1-carboxy-3-phenylpropylamino)-5-carboxymethyl-2-phenyl-2,3-dihydro-1,5-benzothiazepin-4(5H)-one 400 mg of the compound obtained in Example 22 was dissolved in a mixture consisting of 5 ml of ethanol and 2.9 ml of a 1N aqueous solution of sodium hydroxide, and the resulting solution was stirred for 4 hours. After the reaction mixture was concentrated under reduced pressure, it was dissolved in 40 ml of water and a small amount of insoluble matter was removed. Then, the aqueous solution was adjusted to pH 2 with concentrated hydrochloric acid. The precipitated crystals were separated by filtration and washed with water to obtain 280 mg of the desired compound.

The infrared absorption characteristics of this compound were as follows:

$IR_{max}^{KBr}$, cm$^{-1}$: 1730, 1710, 1670, 1470, 1390, 1200, 700.

When analyzed by thin-layer chromatography using a 3:1:1 mixture of n-butanol, water and acetic acid as the developing solvent, this compound gave two spots having $R_f$ values of 0.65 and 0.8, which corresponded to its diastereomers. These diastereomers can be separated, if desired.

EXAMPLE 24

Preparation of 5-t-butoxycarbonylmethyl-3-ethoxycarbonylmethylamino-2-phenyl-2,3-dihydro-1,5-benzothiazepin-4(5H)-one The procedure of Example 21 was repeated except that 1.2 g of the 3-amino-5-t-butoxycarbonylmethyl-2-phenyl-2,3-dihydro-1,5-benzothiazepin-4(5H)-one obtained in Example 20 was reacted with 3.0 g of ethyl glyoxylate.

The resulting concentrate was fractionated and purified by silica gel column chromatography using a 4:1 mixture of benzene and ethyl acetate as the eluent. Thus, there was obtained 1.2 g of the desired compound in the form of an oily material.

When analyzed by thin-layer chromatography using a 4:1 mixture of benzene and ethyl acetate as the developing solvent, this compound exhibited an $R_f$ value of 0.5.

EXAMPLE 25

Preparation of 5-carboxymethyl-3-ethoxycarbonylmethylamino-2-phenyl-2,3-dihydro-1,5-benzothiazepin-4(5H)-one hydrochloride 1.2 g of the compound obtained in Example 24 was dissolved in 10 ml of a 6N solution of hydrogen chloride in dioxane, and the resulting solution was stirred at room temperature for 2 hours. Then, ether was added thereto so as to cause crystallization. The precipitated crystals were separated by filtration and washed with ether to obtain 1.0 g of the desired compound.

The melting point of this compound could not be determined because it decomposed at 202°–205° C.

The infrared absorption characteristics of this compound and the result of its analysis by thin-layer chromatography using a 10:3 mixture of benzene and acetic acid were as follows:

$IR_{max}^{KBr}$, cm$^{-1}$: 1740, 1670, 1380, 1230, 1020, 850, 770.

TLC: $R_f$=0.25.

EXAMPLE 26

Preparation of 5-carboxymethyl-3-carboxymethylamino-2-phenyl-2,3-dihydro-1,5-benzothiazepin-4(5H)-one hydrochloride 410 mg of the compound obtained in Example 25 was dissolved in a mixture consisting of 3.5 ml of a 1N aqueous solution of sodium hydroxide and 5 ml of ethanol, and the resulting solution was stirred for 30 minutes. Then, the solution was adjusted to pH 1–2 with concentrated hydrochloric acid and concentrated to dryness under reduced pressure. The residue was dissolved in ethanol and the insoluble matter was filtered off. After the filtrate was concentrated, ether was added thereto so as to cause crystallization. The precipitated crystals were separated by filtration and washed with ether to obtain 330 mg of the desired compound.

When heated to determine its melting point, this compound began to decompose gradually in the vicinity of 100° C.

The infrared absorption characteristics of this compound and the result of its analysis by thin-layer chromatography using a 3:1:1 mixture of n-butanol, water and acetic acid were as follows:

$IR_{max}^{KBr}$, cm$^{-1}$: 1730, 1670, 1470, 1450, 1400, 1320, 1200, 770.

TLC: $R_f$=0.4.

EXAMPLE 27

Preparation of 5-t-butoxycarbonylmethyl-3-(1-ethoxycarbonylnonylamino)-2-phenyl-2,3-dihydro-1,5-benzothiazepin-4(5H)-one 1.1 g of the compound obtained in Example 20 was reacted with 3.0 g of ethyl 2-ketodecanoate in the same manner as described in Example 21. The reaction product was fractionated and purified by silica gel column chromatography using a 9:1 mixture of benzene and ethyl acetate as the eluent. Thus, there was obtained 1.3 g of the desired compound in the form of an oily material.

When analyzed by thin-layer chromatography using a 8:1 mixture of benzene and ethyl acetate as the developing solvent, this compound gave two spots having $R_f$ values of 0.92 and 0.88, which corresponded to its diastereomers. These diastereomers can be separated, if desired.

EXAMPLE 28

Preparation of 5-carboxymethyl-3-(1-ethoxycarbonylnonylamino)-2-phenyl-2,3-dihydro-1,5-benzothiazepin-4(5H)-one hydrochloride 1.3 g of the oily material obtained in Example 27 was dissolved in 10 ml of a 6N solution of hydrogen chloride in dioxane, and the resulting solution was stirred at room temperature for an hour. Then, ether was added thereto so as to cause crystallization. The precipitated crystals were separated by filtration and washed with ether to obtain 800 mg of the desired compound.

The infrared absorption characteristics of this compound were as follows:

$IR_{max}^{KBr}$, cm$^{-1}$: 2920, 2860, 1730, 1670, 1470, 1450, 1200, 1020.

When analyzed by thin-layer chromatography using a 10:1 mixture of benzene and acetic acid as the developing solvent, this compound gave two spots having $R_f$ values of 0.45 and 0.55, which corresponded to its diastereomers. These diastereomers can be separated, if desired.

EXAMPLE 29

Preparation of 5-carboxymethyl-3-(1-carboxynonylamino)-2-phenyl-2,3-dihydro-1,5-benzothiazepin-4(5H)-one 300 mg of the compound obtained in Example 28 was dissolved in a mixture consisting of 1.6 ml of a 1N aqueous solution of sodium hydroxide and 1 ml of ethanol. The resulting solution was stirred at room temperature for 3 hours and then at 60° C. for an hour. After the addition of ethanol, the precipitated crystals were separated by filtration and washed with ethanol. These crystals were dissolved in a small amount of water and the solution was adjusted to pH 2 with concentrated hydrochloric acid. The precipitated crystals were separated by filtration and washed with water to obtain 170 mg of the desired compound.

The infrared absorption characteristics of this compound were as follows:

IR$_{max}^{KBr}$, cm$^{-1}$: 2920, 2860, 1730, 1710, 1680, 1470, 1450, 1390, 1320, 1210.

When analyzed by thin-layer chromatography using a 10:3 mixture of benzene and acetic acid as the developing solvent, this compound gave two spots having R$_f$ values of 0.15 and 0.25, which corresponded to its diastereomers. These diastereomers can be separated, if desired.

EXAMPLE 30

Pharmacological testing of typical compounds of the invention

The efficacy of the compounds of the present invention can be tested by evaluating their inhibitory effects on the angiotensin converting enzyme (ACE). Using ACE isolated from rabbit lungs, in vitro evaluation of inhibitory effects on ACE activity was carried out according to the method of Cushman [Biochem. Pharmacol., 20, 1637(1971)].

When used at concentrations of 0.1 μM and 0.01 μM, the compound of Example 8 inhibited ACE activity by 77.8% and 14.8%, respectively. Some of the compounds obtained in the other examples were also tested by in vitro evaluation of inhibitory effects on ACE activity and the results thus obtained are summarized in Table 1.

TABLE 1

| Example No. | IC$_{50}$ (μM) |
|---|---|
| 12 | 7.0 |
| 13 | 0.47 |
| 15 | >100 |
| 16 | 8.2 |
| 18 | 0.16 |
| 19 | 0.010 |

The compounds of the present invention can also be tested by evaluating their depressor effects. Such evaluation was carried out by using spontaneously occurring hypertensive rats (SHR). Male rats, aged 20 weeks or more, were fasted for 17 hours. Then, under an unanesthetized condition, the systolic blood pressure of their caudal artery was nonsurgically measured before medication as well as 2,4,6 and 24 hours after medication. Test compounds were orally administered to groups of 3-5 rats showing a systolic blood pressure of 180 mmHg or above.

When the compound of Example 10 was orally administered in a dose of 50 mg/kg, the blood pressure was reduced by 26, 34 and 46 mmHg after the lapse of 2, 4 and 6 hours, respectively. This depressor effect was found to persist even after 24 hours.

Thus, the compounds of the present invention have an inhibitory effect on ACE and a depressor effect, so that they are useful as antihypertensive agents.

What is claimed is:

1. A benzothiazepine compound of the following formula

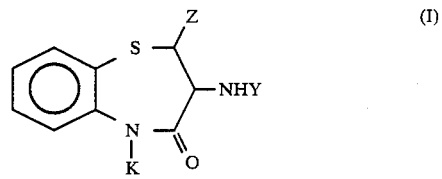

wherein K is hydrogen or a —CH$_2$COOR$_2$ group where R$_2$ is hydrogen or a lower alkyl having 1 to 4 carbon atoms; Z is hydrogen or phenyl when K is a —CH$_2$COOR$_2$ group, and is phenyl when K is hydrogen; and Y is hydrogen, a —CHR$_3$—COOR$_1$ group, an alkanoyl group having 1 to 5 carbon atoms or a —COO(CH$_2$)nR$_4$ where R$_1$ is hydrogen or a lower alkyl having 1 to 4 carbon atoms, R$_3$ is hydrogen, an alkyl group having 1 to 10 carbon atoms, an aralkyl group being benzyl or phenethyl, or an aryl-lower alkyl group where aryl is tolyl or xylyl and the lower alkyl has 1 to 4 carbon atoms, and R$_4$ is an aryl group being phenyl, tolyl or xylyl and n is a whole number of 1 to 10.

2. A benzothiazepine compound as claimed in claim 1 wherein, in the formula (I), K is hydrogen, Z is phenyl and Y is hydrogen, a —CHR$_3$—COOR$_1$ group, an alkanoyl group having 1 to 5 carbon atoms or a —COO(CH$_2$)nR$_4$ group where R$_1$, R$_3$, R$_4$ and n are as previously defined.

3. A benzothiazepine compound as claimed in claim 1 wherein, in the formula (I), K is a —CH$_2$COOR$_2$ group where R$_2$ is as previously defined, Z is hydrogen and Y is hydrogen, a —CHR$_3$—COOR$_1$ group, an alkanoyl group having 1 to 5 carbon atoms or a —COO(CH$_2$)nR$_4$ group where R$_1$, R$_3$, R$_4$ and n are as previously defined.

4. A benzothiazepine compound as claimed in claim 1 wherein, in the formula (I), K is a —CH$_2$COOR$_2$ group where R$_2$ is as previously defined, Z is phenyl and Y is hydrogen, a —CHR$_3$—COOR$_1$ group, an alkanoyl group having 1 to 5 carbon atoms or a —COO(CH$_2$)nR$_4$ group where R$_1$, R$_3$, R$_4$ and n are as previously defined.

5. A benzothiazepine compound as claimed in claim 2 which is 3-amino-2-phenyl-2,3-dihydro-1,5-benzothiazepin-4 (5H)-one or 3-benzyloxycarbonylamino-2-phenyl-2,3-dihydro-1,5-benzothiazepin-4(5H)-one.

6. A benzothiazepine compound as claimed in claim 3 which is 3-amino-5-ethoxycarbonylmethyl-2,3-dihydro-1,5-benzothiazepin-4(5H)-one, 3-amino-5-t-butoxycarbonylmethyl-2,3-dihydro-1,5-benzothiazepin-4(5H)-one, 5-carboxymethyl-3-carboxymethylamino-2,3-dihydro-1,5-benzothiazepin-4(5H)-one, 5-carboxymethyl-3-ethoxycarbonylmethylamino-2,3-dihydro-1,5-benzothiazepin-4(5H)-one, 3-ethoxycarbonylmethylamino-5-t-butoxycarbonylmethyl-2,3-dihydro-1,5-benzothiazepin-4(5H)-one, 5-carboxymethyl-3-(1-carboxyethylamino)-2,3-dihydro-1,5-benzothiazepin-4(5H)-one, 5-carboxymethyl-3-(1-carboxynonylamino)-2,3-dihydro-1,5-benzothiazepin-4(5H)-one, 5-carboxymethyl-3-(1-ethoxycarbonylethylamino)-2,3-dihydro-1,5-benzothiazepin-4(5H)-one, 5-carboxymethyl-3-(1-ethoxycarbonylnonylamino)-2,3-dihydro-1,5-benzothiazepin-4(5H)-one, 5-t-butoxycarbonylmethyl-3-(1-ethoxycarbonylethyl-amino)-2,3-dihydro-1,5-benzothiazepin-4(5H)-one, 3-(1-ethoxycarbonylnonylamino)-5-t-butoxycarbonyl-methyl-2,3-dihydro-1,5-benzothiaze pin-4(5H)-one, 3-(1-carboxy-3-phenylpropylamino)-5-carboxymethyl-2,3-dihydro-1,5-benzothiazepin-4(5H)-one, 5-carboxymethyl-3-(1-ethoxycarbonyl-3-phenylpropylamino)-2,3-dihydro-1,5-benzothiazepin-4(5H)-one or 3-(1-ethoxycarbonyl-3-phenylpropylamino)-5-ethoxycarbonylmethyl-2,3-dihydro-1,5-benzothiazepin-4(5H)-one.

7. A benzothiazepine compound as claimed in claim 4 which is 3-amino-5-t-butoxycarbonylmethyl-2-phenyl-2,3-dihydro-1,5-benzothiazepin-4(5H)-one, 5-carboxymethyl-3-carboxymethylamino-2-phenyl-2,3-dihydro-1,5-benzothiazepin-4 (5H)-one, 5-carboxymethyl-3-ethoxycarbonylmethylamino-2-phenyl -2,3-dihydro-1,5-benzothiazepin-4(5H)-one, 5-t-butoxycarbonylmethyl-3-ethoxycarboxylmethylamino-2-phenyl-2,3-dihydro-1,5-benzothiazepin-4(5H)-one, 5-carboxymethyl-3-(1-car boxynonylamino)-2-phenyl-2,3-dihydro-1,5-benzothiazepin-4 (5H)-one, 5-carboxymethyl-3-(1-ethoxycarbonylnonylamino)-2-phenyl-2,3-dihydro-1,5-benzothiazepin-4(5H)-one, 5-t-butoxycarbonylmethyl-3-(1-ethoxycarbonylnonylamino)-2-phenyl -2,3-dihydro-1,5-benzothiazepin-4(5H)-one, 3-(1-carboxy-3-phenylpropylamino)-3-carboxymethyl-2-phenyl-2,3-dihydro-1,5-benzothiazepin-4(5H)-one, 5-carboxymethyl-3-(1-ethoxycarbonylmethyl-3-phenyl-propylamino)-2-phenyl-2,3-dihydro-1,5-benzothiazepin-4(5H)-one or 5-t-butoxycarbonylmethyl-3-(1-ethoxycarbonyl-3-phenylpropylamino)-2-phenyl-2,3-dihydro-1,5-benzothiazepin-4(5H)-one.

8. A process for preparing benzothiazepine compound of the following formula

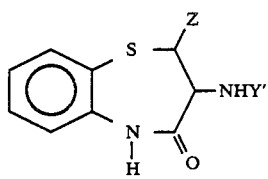
(IV)

wherein Z is hydrogen or phenyl and Y' is hydrogen, an acyl group being alkanoyl having 1 to 5 carbon atoms including trifluoroacetyl and trichloroacetyl or benzoyl, a —COO(CH$_2$)nR$_4$ group where R$_4$ is an acyl group being phenyl, tolyl or xylyl and n is a whole number of 1 to 10, benzyloxycarbonyl group having a substitute or substitutes of P-methoxy, P-chloro, P-nitro, 3,5-dimethoxy or 3,4,5-trimethoxy, or an alkoxycarbonyl group being t-butoxycarbonyl, which comprises reacting a compound of the following formula $$\underset{ZCH=C-COOR_5}{\overset{NHY^2}{|}} \qquad (II)$$

wherein Z is as previously defined, Y$^2$ is the same as defined in Y' except that hydrogen is excluded and R$_5$ is hydrogen, with 2-aminobenzenethiol to form a compound of the following formula

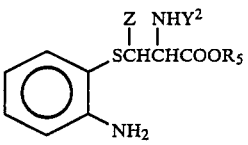
(III)

wherein Z, Y$^2$ and R$_5$ are as previously defined; and then cyclizing the compound of the formula (III) with or without subsequent elimination of Y$^2$ group.

9. A process for preparing benzothiazepine compound of the following formula

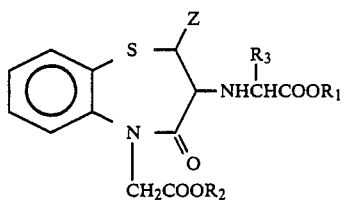
(IX)

wherein Z is hydrogen or phenyl, R$_1$ is hydrogen or a lower alkyl group having 1 to 4 carbon atoms, R$_2$ is hydrogen or a lower alkyl group 1 to 4 carbon atoms, and R$_3$ is hydrogen, an alkyl group of 1 to 10 carbon atoms, an aralkyl group being benzyl or phenethyl or an aryl-lower alkyl group where aryl is tolyl or xylyl and lower alkyl has 1 to 4 carbon atoms, which comprises reacting a compound of the following formula $$XCH_2COOR_2 \qquad (V)$$

wherein X is a halogen and R$_2$ is as previously defined, with

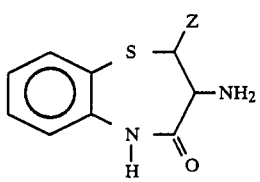
(VI)

wherein Z is as previously defined, to form a compound of the following formula

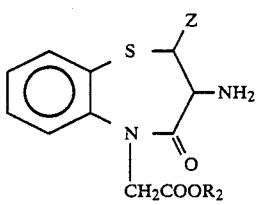
(VII)

wherein Z and R$_2$ are as previously defined; and then reacting the compound of the formula (VII) with a compound of the following formula $$R_3COCOOR_1 \qquad (VIII)$$

wherein R$_1$ and R$_3$ are as previously defined, in the presence of a reducing agent or with subsequent reduction by means of a reducing agent.

* * * * *